US00PP28007P3

(12) United States Plant Patent
Davey et al.

(10) Patent No.: US PP28,007 P3
(45) Date of Patent: May 9, 2017

(54) ***HELLEBORUS* PLANT NAMED 'EPB 32'**

(50) Latin Name: *Helleborus×hybridus*
Varietal Denomination: EPB 32

(71) Applicants: Rodney Davey, Axminster (GB); Lynda Windsor, Axminster (GB)

(72) Inventors: Rodney Davey, Axminster (GB); Lynda Windsor, Axminster (GB)

( * ) Notice: Subject to any disclaimer, the term of this patent is extended or adjusted under 35 U.S.C. 154(b) by 3 days.

(21) Appl. No.: 14/756,540

(22) Filed: Sep. 15, 2015

(65) Prior Publication Data

US 2017/0079183 P1 Mar. 16, 2017

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'EPB 32', characterized by its upright and mounding plant habit; uniform, continuous and freely flowering habit; relatively large dark purple-colored flowers that are held above the foliar plane on relatively long peduncles; and good garden performance.

2 Drawing Sheets

Botanical designation: *Helleborus×hybridus*.
Cultivar denomination: 'EPB 32'.

BACKGROUND OF THE INVENTION

The present invention relates to a new and distinct cultivar of *Helleborus* plant, botanically known as *Helleborus×hybridus* and hereinafter referred to by the name 'EPB 32'.

The new *Helleborus* plant is a product of a planned breeding program conducted by the Inventors in Devon, United Kingdom. The objective of the breeding program was to create new freely-flowering *Helleborus* plants with strong peduncles that hold numerous attractive flowers above the foliar plane.

The new *Helleborus* plant originated from a cross-pollination conducted by the Inventors in Devon, United Kingdom on Jan. 23, 2008 of a proprietary seedling selection of *Helleborus×hybridus* identified as code designation BGE-8855, as the female, or seed, parent, not patented, with a proprietary seedling selection of *Helleborus×hybridus* identified as code designation EDB-469, as the male, or pollen, parent, not patented. The new *Helleborus* plant was discovered and selected by the Inventors as a single flowering plant from within the progeny of the stated cross-pollination grown in a controlled greenhouse environment in Devon, United Kingdom on Feb. 16, 2010.

Asexual reproduction of the new *Helleborus* plant by tissue culture in a controlled greenhouse environment in Roelofarendsveen, The Netherlands since Apr. 10, 2013, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'EPB 32'. These characteristics in combination distinguish 'EPB 32' as a new and distinct *Helleborus* plant:

1. Upright and mounding plant habit.
2. Uniform, continuous and freely flowering habit.
3. Relatively large dark purple-colored flowers that are held above the foliar plane on relatively long peduncles.
4. Good garden performance.

Plants of the new *Helleborus* differ from plants of the female parent selection in the following characteristics:

1. Plants of the new *Helleborus* are shorter than plants of the female parent selection.
2. Plants of the new *Helleborus* and the female parent selection differ in flower color as plants of the female parent selection have lighter purple-colored flowers.

Plants of the new *Helleborus* differ from plants of the male parent selection in the following characteristics:

1. Plants of the new *Helleborus* are shorter than plants of the male parent selection.
2. Plants of the new *Helleborus* and the male parent selection differ in flower color as plants of the male parent selection have lighter purple-colored flowers.

Plants of the new *Helleborus* can be compared to plants of *Helleborus×hybridus* 'ABCRD02', disclosed in U.S. Plant Pat. No. 24,720. In side-by-side comparisons conducted in Devon, United Kingdom, plants of the new *Helleborus* differed from plants of 'ABCRD02' in the following characteristics:

1. Plants of the new *Helleborus* were broader than plants of 'ABCRD02'.
2. Leaves of plants of the new *Helleborus* were smaller and lighter green in color than leaves of plants of 'ABCRD02'.

3. Plants of the new *Helleborus* were more freely flowering than plants of 'ABCRD02'.
4. Plants of the new *Helleborus* and 'ABCRD02' differed in flower color as plants of 'ABCRD02' had lighter purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'EPB 32' grown in a container.

The photograph on the second sheet is a close-up view of a typical flower of 'EPB 32'.

DETAILED BOTANICAL DESCRIPTION

The aforementioned photographs and following observations, measurements and values describe plants grown during the winter in three-liter containers in an outdoor nursery in Boijl, The Netherlands and under cultural practices typical of commercial *Helleborus* production. During the production of the plants, day temperatures ranged from 0° C. to 10° C. and night temperatures ranged from −15° C. to 0° C. Plants were one year old when the photographs and the description were taken. In the following description, color references are made to The Royal Horticultural Society Colour Chart, 2001 Edition, except where general terms of ordinary dictionary significance are used.

Botanical classification: *Helleborus hybridus* 'EPB 32'.

Parentage:

*Female, or seed, parent*.—Proprietary seedling selection of *Helleborus×hybridus* identified as code designation BGE-8855, not patented.

*Male, or pollen, parent*.—Proprietary seedling selection of *Helleborus×hybridus* identified as code designation EDB-469, not patented.

Propagation:

*Type*.—By tissue culture.

*Time to initiate roots, summer*.—About 15 days at temperatures about 22° C. to 25° C.

*Time to produce a rooted young plant, summer*.—About two months at temperatures about 20° C.

*Root description*.—Fleshy, vigorous; typically white to brown in color, actual color of the roots is dependent on substrate composition, water quality, fertilizer type and formulation, substrate temperature and physiological age of roots.

Plant description:

*Plant and growth habit*.—Herbaceous perennial; upright and mounding plant habit with flowers held above the foliar plane; moderately vigorous to vigorous growth habit.

*Plant height*.—About 25 cm to 35 cm.

*Plant diameter* (*area of spread*).—About 30 cm to 40 cm.

*Stems*.—Strength: Strong. Aspect: Mostly upright. Texture: Smooth, glabrous. Luster: Shiny. Color: Close to 146B with spots, close to 187A.

Leaf description:

*Arrangement*.—Leaves arranged alternately in a basal rosette; leaves palmately compound with three to five leaflets per leaf.

*Leaflet length*.—About 10 cm to 15 cm.

*Leaflet width*.—About 7 cm to 10 cm.

*Leaflet shape*.—Ovate to lanceolate.

*Leaflet apex*.—Acute.

*Leaflet base*.—Acute.

*Leaflet margin*.—Serrate.

*Leaflet texture, upper and lower surfaces*.—Smooth, glabrous; leathery.

*Leaflet luster, upper surface*.—Shiny.

*Leaflet luster, lower surface*.—Somewhat shiny.

*Leaflet venation pattern*.—Pinnate.

*Leaflet color*.—Developing leaves, upper surface: Close to 137A; towards the center, slightly overlain with close to 187B. Developing leaves, lower surface: Close to 146A overlain with close to 187A. Fully expanded leaves, upper surface: Close to 139A; spots, close to 138B; towards the center, slightly overlain with close to N187C; venation, close to 139C, proximally, close to 187A. Fully expanded leaves, lower surface: Close to 147B overlain with close to 187A; venation, close to 137B and 187A.

*Petioles*.—Length: About 10 cm to 15 cm. Diameter: About 5 mm to 7 mm. Texture, upper and lower surfaces: Smooth, glabrous. Color, developing leaves, upper and lower surfaces: Close to 146A; spots, close to N186C. Color, fully expanded leaves, upper and lower surfaces: Close to 146A; spots, close to N186A.

Flower description:

*Flower shape and habit*.—Single rotate flowers arranged in loosely branched cymes; freely flowering habit with typically about 10 to 25 flowers developing per cyme and up to 40 flowers developing per cyme in the second year of growth; flowers facing outwardly and somewhat drooping.

*Fragrance*.—None detected.

*Natural flowering season*.—Plants begin flowering about two months after planting; plants flower from January until March in the United Kingdom.

*Flower longevity on the plant*.—About two to three months; flowers persistent.

*Inflorescence height*.—About 25 cm to 30 cm.

*Inflorescence diameter*.—About 35 cm to 45 cm.

*Flower buds*.—Length: About 1 cm to 3 cm. Diameter: About 1 cm to 2 cm. Shape: Ovoid. Color: Close to N79B.

*Flower diameter*.—About 6 cm to 8 cm.

*Flower depth* (*height*).—About 2 cm to 3 cm.

*Petals*.—None observed; transformed into nectaries.

*Sepals*.—Quantity and arrangement: Five arranged in a single whorl. Length: About 3 cm to 4 cm. Width: About 3.5 cm to 4.5 cm. Shape: Ovate to obovate. Apex: Obtuse and occasionally emarginate. Base: Rounded. Margin: Mostly entire. Texture, upper and lower surfaces: Smooth, glabrous. Luster, upper and lower surfaces: Matte. Color: When opening and fully opened, upper surface: Close to N79A; towards the center and base, close to 146C; spots, close to 79A; color does not change with development. When opening and fully opened, lower surface: Close to N79B; color does not change with development.

*Peduncles*.—Length: About 10 cm to 15 cm. Diameter: About 5 mm to 10 mm. Strength: Strong. Aspect: Mostly upright. Texture: Smooth, glabrous. Color: Close to 146B; spots, close to 187A.

*Pedicels*.—Length: About 6 cm to 12 cm. Diameter: About 3 mm to 4 mm. Aspect: About 10° from peduncle axis. Strength: Strong. Texture: Smooth, glabrous. Color: Close to 146B; spots, close to 187A.

*Reproductive organs*.—Stamens: Quantity per flower: About 60. Filament length: About 1 cm to 1.5 cm. Filament color: Close to 155D. Anther shape: Ovate. Anther length: About 2 mm. Anther color: Close to 4B. Pollen amount: Scarce. Pollen color: Close to 4B. Pistils: Quantity per flower: About five. Pistil length: About 2 cm. Stigma shape: Club-shaped. Stigma color: Close to 4D. Style length: About 1.5 cm. Style color: Close to N79B. Ovary color: Close to N79B.

*Nectaries*.—Quantity per flower: About 10 to 15. Length: About 5 mm to 8 mm. Width: About 3 mm to 5 mm. Shape: Funnelform. Color: Close to N144C.

*Seeds and fruits*.—Seed and fruit development have not been observed on plants of the new *Helleborus*.

Garden performance: Plants of the new *Helleborus* have been observed to have good garden performance and to tolerate rain, wind and temperatures ranging from about −20° C. to about 35° C.

Pathogen & pest resistance: Plants of the new *Helleborus* have not been observed to be resistant to pathogens and pests common to *Helleborus* plants.

It is claimed:

1. A new and distinct *Helleborus* plant named 'EPB 32' as illustrated and described.

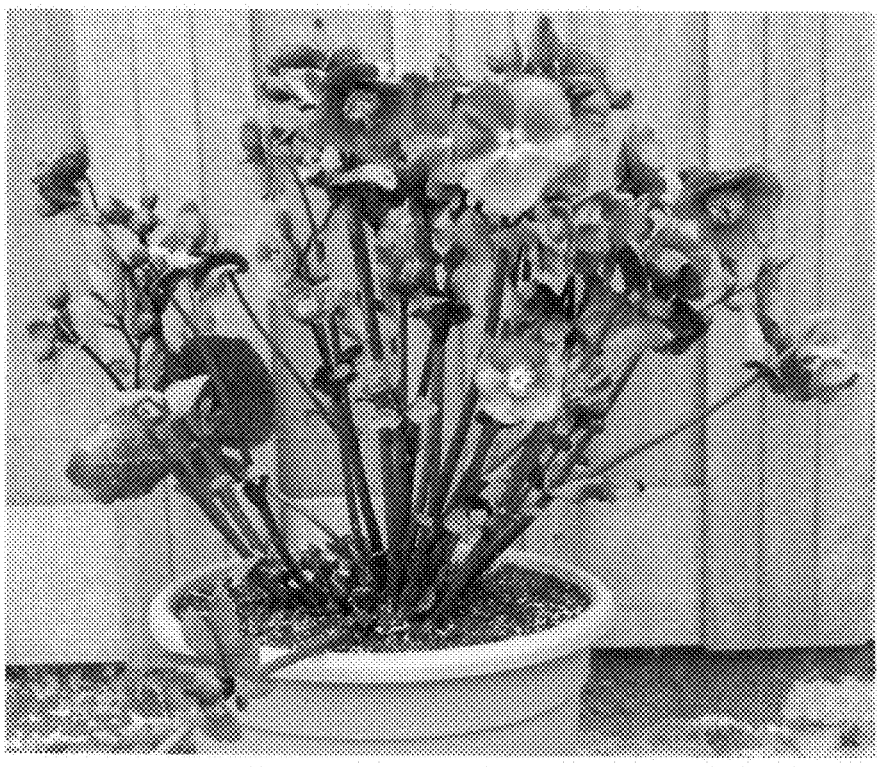

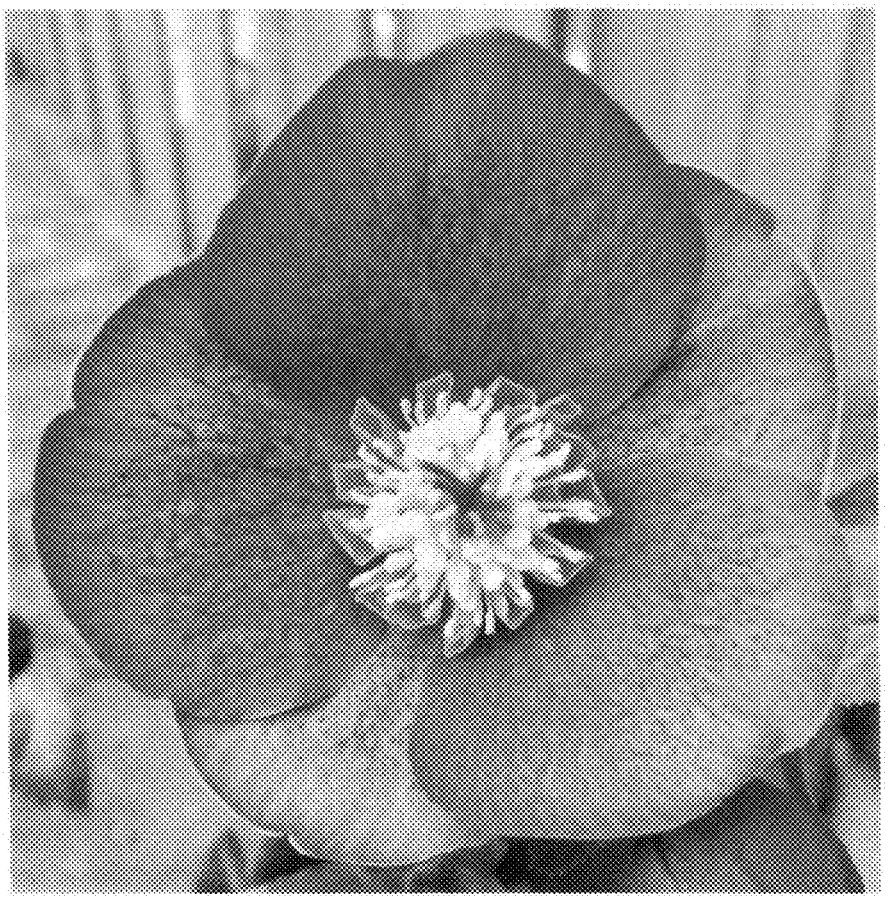

* * * * *